(12) United States Patent
Pigeat et al.

(10) Patent No.: US 7,880,048 B2
(45) Date of Patent: Feb. 1, 2011

(54) PROCESS FOR PRODUCING PROPYLENE IN THE PRESENCE OF A MACROPOROUS CATALYST IN THE FORM OF SPHERICAL BEADS

(75) Inventors: Brigitte Pigeat, Lyons (FR); Vincent Coupard, Vaulx en Velin (FR); Sylvie Maury, Charly (FR); Serge Drouet, Montanay (FR)

(73) Assignee: IFP, Rueil Malmaison Cedex (FR)

( * ) Notice: Subject to any disclaimer, the term of this patent is extended or adjusted under 35 U.S.C. 154(b) by 719 days.

(21) Appl. No.: 11/892,561

(22) Filed: Aug. 23, 2007

(65) Prior Publication Data

US 2009/0088595 A1   Apr. 2, 2009

(30) Foreign Application Priority Data

Aug. 24, 2006  (FR) ................... 06 07494

(51) Int. Cl.
C07C 4/06 (2006.01)
(52) U.S. Cl. ...................... 585/648; 585/653
(58) Field of Classification Search ............... 585/648, 585/653; 502/64, 77
See application file for complete search history.

(56) References Cited

U.S. PATENT DOCUMENTS

2004/0064008 A1 * 4/2004 Maurer et al. ............... 585/640
2006/0063662 A1 * 3/2006 Hata et al. ..................... 502/4
2006/0063957 A1 * 3/2006 Louret et al. ................ 585/653

FOREIGN PATENT DOCUMENTS

| EP | 1 637 575 | 3/2006 |
| EP | 1 777 284 A1 | 4/2007 |
| FR | 2 879 620 | 6/2006 |
| WO | WO 01/04237 A2 | 1/2001 |
| WO | WO 01/04237 A3 | 1/2001 |
| WO | WO 03/078364 A1 | 9/2003 |

OTHER PUBLICATIONS

Partial French Search Report issued in FR 0607494 dated May 21, 2007.

* cited by examiner

*Primary Examiner*—Tam M Nguyen
(74) *Attorney, Agent, or Firm*—Millen, White, Zelano & Branigan, P.C.

(57) ABSTRACT

A process for once-through conversion of a hydrocarbon feed comprising at least olefins containing 4 carbon atoms and at least olefins containing 5 carbon atoms is described for the production of propylene, said process comprising passing said feed into at least one reaction unit provided with at least one catalyst in the form of spherical beads with a diameter in the range 1 to 3 mm, each of said spherical beads comprising at least one zeolite and at least one alumina-based support and having a pore distribution such that the macroporous volume, measured by mercury porosimetry, is in the range 0.10 to 0.20 ml/g and the mesoporous volume, measured by mercury porosimetry, is in the range 0.25 to 0.35 ml/g.

13 Claims, 1 Drawing Sheet

PROCESS FOR PRODUCING PROPYLENE IN THE PRESENCE OF A MACROPOROUS CATALYST IN THE FORM OF SPHERICAL BEADS

FIELD OF THE INVENTION

The present invention relates to the field of the production of propylene from a hydrocarbon feed comprising at least olefins containing 4 carbon atoms and at least olefins containing 5 carbon atoms. Said hydrocarbon feed advantageously derives either from the olefinic C4/C5 cut from a steam cracking unit, or from olefinic C4 cuts and gasoline from a fluid catalytic cracking (FCC) unit, or from a mixture of said cuts from steam cracking and fluid catalytic cracking. The propylene production process of the invention uses at least one catalyst in the form of spherical beads prepared in the presence of a porogen to create macroporous domains in the porosity of each of said beads.

PRIOR ART

A number of patents and publications have addressed propylene production.

In particular, the process disclosed in International patent application WO-A-01/04237 is a one-step propylene production process carried out using light olefins and using a catalyst comprising a ZSM-5 zeolite. That process uses a fluidized bed technique which is expensive as regards investment, and also the process is relatively difficult to carry out. It also results in substantial losses of catalyst by attrition. Zeolites with structure type MFI, in particular ZSM-5 zeolite, are frequently used in catalysts to carry out a propylene production process (WO-A-99/29805, EP-A-0 921 181, EP-A-0 921 179, EP-A-1 195 424). They generally have a high Si/Al ratio (180 to 1000) to limit hydrogen transfer reactions responsible for the production of dienes and aromatics.

In general, even though all of the processes for propylene production described above produce satisfactory propylene yields, the production of by-products, in particular gasoline and C4 compounds which are rich in olefins including isobutene, is generally non-negligible, to the detriment of selectivity for the desired product, namely propylene.

The present invention proposes a propylene production process which limits the production of said unwanted by-products to boost the selectivity of the reaction towards propylene and thus increase the propylene/isobutene ratio to satisfy market trends. The propylene production process of the invention also has the advantage of being cheaper in terms of energy consumption compared with prior art processes: in fact, it has surprisingly been discovered that to achieve identical propylene production (identical propylene yield) when the reaction unit functions in moving bed mode, the process of the invention necessitates a smaller quantity of recycled C4/C5 olefins than that necessitated by prior art processes.

DESCRIPTION OF THE INVENTION

The present invention provides a process for once-through conversion of a hydrocarbon feed comprising at least olefins containing 4 carbon atoms and at least olefins containing 5 carbon atoms for the production of propylene, said process comprising passing said feed into at least one reaction unit provided with at least one catalyst in the form of spherical beads with a diameter in the range 1 to 3 mm, each of said spherical beads comprising at least one zeolite and at least one alumina-based support and having a pore distribution such that the macroporous volume, measured by mercury porosimetry, is in the range 0.10 to 0.20 ml/g and the mesoporous volume, measured by mercury porosimetry, is in the range 0.25 to 0.35 ml/g.

The process of the invention envisages the production of propylene by conversion of a hydrocarbon feed comprising at least olefins containing 4 carbon atoms per molecule and at least olefins containing 5 carbon atoms per molecule. The process of the invention is termed a once-through conversion process for said feed as transformation of said feed for the production of propylene is carried out in a single step using at least one reaction unit which may contain a plurality of reactors to maintain the reaction temperature constant or to ensure that the temperature does not deviate by more than ±20° C. with respect to said desired reaction temperature.

According to the invention, said feed treated in the reaction unit for the production of propylene advantageously derives either from the olefinic C4/C5 cut from a steam cracking unit or from olefinic C4 cuts and gasoline from a fluid catalytic cracking unit (FCC), or from a mixture of said cuts derived from steam cracking and fluid catalytic cracking. Steam cracking corresponds to cracking various hydrocarbon cuts with steam, usually a naphtha cut with a boiling point in the range 100° C. to 350° C., and produces mainly olefins, essentially ethylene and propylene, but also olefins with a higher number of carbon atoms. The C4/C5 olefinic cut from a steam cracking unit is generally produced with a yield which, depending on the feeds and the operating conditions, may be up to 10% by weight, and cannot be upgraded immediately. It constitutes the feed of choice for conversion into propylene in the process of the invention.

With an olefinic C4 cut from a steam cracking unit which is advantageously used in the process of the invention, said cut may advantageously be an unrefined C4 cut from a steam cracking unit and/or an olefinic C4 cut obtained after treatment of an unrefined C4 cut from a steam cracking unit, said treatment consisting of extracting diolefinic compounds, in particular butadiene, present in said unrefined C4 cut, by absorption into a solvent. That type of process for extracting diolefinic compounds, in particular butadiene, is described, for example, in the work entitled "Procédés de pétrochimie [Petrochemical processes], volume 1, Chapter III, page 224, 1985, Technip (A Chauvel-G Lefebvre-L Castex). Before being introduced into said at least one reaction unit provided with at least said catalyst and carrying out propylene transformation, said olefinic C4 cut from a steam cracking unit is advantageously introduced into at least one unit for selective hydrogenation of polyunsaturated diene and acetylene residue type compounds. Passing said olefinic C4 cut from a steam cracking unit into said selective hydrogenation unit not only allows conversion of the diolefins into mono-olefins, but also the elimination of acetylenic compounds which are converted into mono-olefins. Said selective hydrogenation step is optional when the olefinic C4 cut from the steam cracking unit has undergone a treatment consisting of extracting the diolefinic compounds, in particular butadiene, present in said unrefined C4 cut, by absorption into a solvent as indicated above, and the effluent from said extraction unit has a diolefinic compound content of less than 10000 ppm. When the amount of diolefinic compounds in the olefinic C4 cut from the steam cracking unit to be treated is high, i.e. generally over 1.5% by weight, said selective hydrogenation step is carried out using a plurality of reactors in series, for example two, the effluent comprising the unconverted diolefins advantageously being recycled at least in part to the inlet to the selective hydrogenation unit to control the overall temperature rise in the reaction. The selective hydrogenation unit is operated in the presence of hydrogen which is introduced into said unit in a quantity of 5% to 30% molar above the stoichiometric quantity of the reaction, preferably 10% to 20% molar above the stoichiometric quantity, the $H_2$/(diolefins+acetylenes) mole ratio thus being in the range 1.05 to 1.30, preferably in the range 1.1 to 1.2.

The catalyst(s) used to carry out the selective hydrogenation step is(are) generally formed by at least one group VIII metal, preferably nickel or palladium, deposited on at least one support based on refractory oxide such as alumina. When said group VIII metal is palladium, the amount of said metal is advantageously in the range 0.1% to 5% by weight, preferably in the range 0.2% to 0.5% by weight, of catalyst. When said group VIII metal is nickel, the amount of that metal is advantageously in the range 5% to 25% by weight, preferably in the range 7% to 20% by weight, of catalyst. Said catalyst has a specific surface area $S_{BET}$ which can limit the polymerization reactions at the surface of the selective hydrogenation catalyst, said specific surface area being in the range 5 to 140 $m^2/g$.

The selective hydrogenation reaction is preferably carried out in one or more fixed bed reactor(s), generally in downflow mode for the first reactor carrying out the principal reaction, i.e. at least 60% of the total conversion (this is the case when the effluent to be converted contains more than 1.5% by weight of diolefins), and generally in co-current upflow mode for the secondary reactors carrying out the finishing phase of the reaction. The operating conditions in the selective hydrogenation unit are selected so that the effluent from said unit remains in the liquid state: the temperature in said unit is in the range 20° C. to 150° C., the total pressure is in the range 0.5 bars to 4 MPa. The HSV (ratio of the hourly volume flow rate at 15° C. of fresh liquid feed over the loaded volume of catalyst) is in the range 4 to 10 $h^{-1}$. The amount of polyunsaturated compounds (diolefins and/or acetylenes) of the effluent leaving the selective hydrogenation step is in the range 10 ppm to 4000 ppm and is preferably in the range 50 ppm to 1000 ppm.

The olefinic gasoline cut from a steam cracking unit which is advantageously used in the process of the invention comprises mainly aromatic compounds (benzene, toluene, xylenes, ethylbenzene), cyclodiolefins and diolefins (principally isoprene), alkenyl aromatics (aromatic compounds with an alkyl group having an unsaturated bond, such as styrene), paraffins and olefins, the aromatic compounds representing 40% to 60% by weight of said cut, the cyclodiolefins and diolefins (principally isoprene) representing 20% to 30% by weight of said cut. C5 hydrocarbons represent 10% to 40% by weight of said gasoline cut, preferably 20% to 25% by weight of said gasoline cut. Polyunsaturated compounds (dienes and acetylenes) present in said initial olefinic gasoline cut are preferably eliminated, at least in part, by passing said cut into at least one selective hydrogenation unit, which is provided with at least one catalyst generally formed by at least one group VIII metal, preferably nickel or palladium, deposited on at least one support based on refractory oxide such as alumina. When said group VIII metal is palladium, the amount of said metal is advantageously in the range 0.1% to 5% by weight, preferably 0.2% to 0.6% by weight of catalyst. When said group VIII metal is nickel, the amount of said metal is advantageously in the range 5% to 25% by weight, preferably 7% to 20% by weight. Said catalyst has a specific surface area $S_{BET}$ which can limit polymerization reactions at the surface of the selective hydrogenation catalyst, said specific surface area being in the range 5 to 140 $m^2/g$.

The selective hydrogenation unit is operated in the presence of hydrogen which is introduced into said unit in a quantity of 100 to 500 normal $m^3$ of gas/$m^3$ of liquid feed at 15° C. The quantity of hydrogen used is in excess to encourage the conversion of less reactive species, for example styrene compounds, present in said olefinic gasoline cut derived from the steam cracking unit.

The selective hydrogenation reaction is preferably carried out in one or more fixed bed reactor(s), generally in downflow mode for the first reactor carrying out the principal reaction, i.e. carrying out at least 60% of the total conversion (this is the case when the effluent to be converted contains more than 1.5% by weight of diolefins). The operating conditions in the selective hydrogenation unit are selected so that the effluent from said unit remains in the liquid state: the temperature in said unit is in the range 20° C. to 200° C.; the total pressure is in the range 0.5 to 4 MPa and the hydrogen pressure is less than 2 MPa. The HSV (ratio of the hourly volume flow rate at 15° C. of fresh liquid feed to the volume of loaded catalyst) is in the range 0.3 to 6 $h^{-1}$. The effluent leaving said selective hydrogenation unit is advantageously introduced into at least one separation column to recover a light fraction essentially formed (between 10% and 40% of the initial gasoline cut) from compounds containing 5 carbon atoms including at least 60% by weight of C5 mono-olefins (pentene and isopentene), said light fraction possibly also containing C5 paraffins as well as C6 and C4 hydrocarbons. A heavy fraction mainly formed from aromatic compounds (benzene, toluene, xylene, ethylbenzene), olefinic compounds (C6 olefins) and cyclo-olefinic compounds (dihydro-dicyclopentadiene and alkylated derivatives) is extracted from the bottom of the separation column. Said light fraction is such that it is used to carry out the process of the invention.

"FCC" denotes fluidized bed catalytic cracking of oil fractions with a boiling point of more than about 350° C., generally a vacuum distillate, possibly deasphalted oil or an atmospheric residue. The gasoline from a FCC corresponds to a cut with a boiling point which is generally in the range 20° C. to 250° C. This gasoline is relatively rich in unsaturated compounds of the olefinic, mono-olefinic and diolefinic type (between 20% and 50% by weight), and contains sulphur in amounts of up to a few % by weight. Said gasoline cut from FCC, a third of the weight of which is constituted by a cut boiling between 20° C. and 60° C., is processed in at least one selective hydrogenation unit, SHU. Separation of light compounds, or topping, is carried out following the SHU step to extract a cut boiling between 20° C. and 60° C. and mainly, i.e. at least 15% by weight, preferably at least 30% by weight, comprising hydrocarbon compounds containing 5 carbon atoms. This light cut is rich in mono-olefins (pentene and isopentene) and constitutes the feed of choice for carrying out the process of the invention. The catalyst(s) used to carry out the selective hydrogenation step (SHU) is (are) generally formed from at least one group VIII metal, preferably nickel or palladium, deposited on at least one support based on refractory oxide such as alumina. When said group VIII metal is palladium, the amount of this metal is advantageously in the range 0.1% to 5% by weight, preferably in the range 0.2% to 0.6% by weight of catalyst. When said group VIII metal is nickel, the amount of this metal is advantageously in the range 5% to 25% by weight, preferably in the range 7% to 20% by weight and the catalyst is sulphurized to passivate the surface nickel atoms. Said selective hydrogenation catalyst has a specific surface area $S_{BET}$ which can limit polymerization reactions on the surface of the selective hydrogenation catalyst, said specific surface area being in the range 5 to 140 $m^2/g$. Hydrogen is introduced into the selective hydrogenation unit in a quantity of 5% to 30% molar above the stoichiometric reaction quantity, preferably 10% to 20% molar above the stoichiometric quantity. The operating conditions in the selective hydrogenation unit are selected so that the effluent from said unit remains in the liquid state: the temperature in said unit is in the range 120° C. to 200° C., the total pressure is in the range 0.5 to 4 MPa. The HSV (ratio of the hourly volume flow rate at 15° C. of the fresh liquid feed over the loaded volume of catalyst) is in the range 4 to 10 $h^{-1}$.

The C4 cut from FCC corresponds to a hydrocarbon fraction mainly composed, i.e. at least 80% by weight, of molecules containing 4 carbon atoms produced by the FCC. This cut generally represents 4% to 10% by weight of the initial feed treated by FCC. It comprises at least 30% by weight of olefins, preferably at least 60% by weight, the proportion of mono-olefins being greatest with respect to the diolefins. The mono-olefins generally represent at least 98% of the total olefinic fraction. Said C4 cut from FCC also contains hetero-elements, generally sulphur present in a quantity representing 5 to 50 ppm, in particular in the form of mercaptans, and/or nitrogen in the ammoniacal and/or acetonitrile form, generally present in a quantity representing 5 to 30 ppm. At least part of the sulphur containing compounds, in particular in the form of mercaptans, are extracted from said FCC cut in which they are present by treatment of said cut in at least one contacting unit, consisting of bringing sodium hydroxide into contact with said cut containing said sulphur containing compounds, at least one water washing unit and at least one coalescer being located downstream of said contacting unit. The contacting unit is, for example, provided with Merox® extraction or sulfrex®: it is an adsorption column containing an aqueous solution of sodium hydroxide having a concentration of close to 10% molar. This step is carried out at a sufficient pressure so that the reagents remain liquid and at a temperature in the range 40° C. to 100° C. The effluent from the contacting step preferably does not contain more than 3 ppm of sulphur. It advantageously constitutes at least part of the feed introduced into the reaction zone carrying out the transformation into propylene. The water washing unit, placed downstream of the contacting unit, eliminates at least 80% by weight of the nitrogen containing species present in the C4 cut from FCC. The contacting step is particularly advantageous when the sulphur content of the C4 cut from FCC is at least 5 ppm.

The effluent depleted in sulphur containing compounds is then advantageously introduced into at least one selective hydrogenation unit. Hydrogen is introduced into the selective hydrogenation unit in a quantity of 5% to 30% molar above the stoichiometric reaction quantity, preferably 10% to 20% molar above the stoichiometric quantity, the $H_2$/diolefins mole ratio then being in the range 1.05 to 1.3, preferably 1.1 to 1.2.

The catalyst(s) to carry out the selective hydrogenation step is (are) generally formed by at least one group VIII metal, preferably nickel or palladium, deposited on at least one support based on a refractory oxide such as alumina. When said group VIII metal is palladium, the amount of this metal is advantageously in the range 0.1% to 5% by weight, preferably in the range 0.2% to 0.6% by weight of catalyst. When said group VIII metal is nickel, the amount of this metal is advantageously in the range 5% to 25% by weight, preferably 7% to 20% by weight. Said catalyst has a specific surface area $S_{BET}$ which can limit polymerization reactions at the surface of the selective hydrogenation catalyst, said surface area being in the range 5 to 140 $m^2/g$.

The selective hydrogenation reaction is preferably carried out in one or more fixed bed reactors, generally in downflow mode for the first reactor when the effluent to be converted, depleted in sulphur containing compounds, contains more than 1.5% by weight of diolefins, and generally in upflow co-current mode for the secondary reactors when said effluent to be converted, depleted in sulphur containing compounds, contains less than 1.5% by weight of diolefins. The operating conditions in the selective hydrogenation unit are selected so that the effluent from said unit remains in the liquid state: the temperature in said unit is in the range 20° C. to 150° C.; the total pressure is in the range 0.5 to 4 MPa. The HSV (volume ratio of the hourly flow rate at 15° C. of fresh liquid feed to the loaded volume of catalyst) is in the range 4 to 10 $h^{-1}$.

The hydrocarbon feed comprising at least olefins containing 4 carbon atoms and at least olefins containing 5 carbon atoms which is introduced into said reaction unit for propylene production is mainly composed of mono-olefinic compounds containing 4 or 5 carbon atoms, i.e. 20% to 100% by weight, preferably 25% to 60% by weight of mono-olefinic compounds containing 4 or 5 carbon atoms. Said hydrocarbon feed may also contain diolefins containing 4 and/or 5 carbon atoms preferably representing no more than 1% by weight of said hydrocarbon feed entering the reaction zone. Olefinic compounds containing more than 5 carbon atoms per molecule may also be present. Compounds containing at least one hetero-element, in particular sulphur containing compounds, may be present in small quantities: they represent no more than 100 ppm of said hydrocarbon feed entering said reaction zone.

A feed with such a composition is advantageously obtained by mixing a C4 cut and a C5 cut derived from a steam cracking unit, by mixing a C4 cut and a gasoline cut from a fluid catalytic cracking unit (FCC), by mixing a C4 cut from a steam cracking unit and a gasoline cut from a fluid catalytic cracking unit (FCC), by mixing a C4 cut from a fluid catalytic cracking unit (FCC) and a C5 cut from a steam cracking unit or by mixing C4/C5 cuts from a steam cracking unit and C4 cuts and gasoline from a fluid catalytic cracking unit (FCC), said cuts from a steam cracking unit and those from a catalytic cracking unit having the characteristics of the cuts described above and pre-treated using the processes described above (selective hydrogenation, contacting process).

The reaction unit carrying out conversion of said hydrocarbon feed for the production of propylene and provided with at least said catalyst is used at a temperature in the range 450° C. to 580° C., at an operating pressure in the range 0.01 to 0.5 MPa and a WHSV (hourly flow rate mass/catalyst mass) in the range 1 to 20 $h^{-1}$. Said catalyst is used in said reaction unit operating either in moving bed or in fixed bed move, preferably in fixed bed mode.

The effluent from said reaction unit is fractionated to separately recover at least one first fraction containing the desired propylene, at least one second fraction including hydrogen, at least one third fraction including non aromatic hydrocarbon compounds containing 4, 5 and/or 6 carbon atoms per molecule and at least one fourth fraction comprising aromatic compounds containing at least 6 atoms and/or heavy hydrocarbon compounds containing at least 7 carbon atoms per molecule and generally at least 9 carbon atoms per molecule.

Said first fraction containing propylene also generally comprises 5% to 7% by weight of propane. A propylene separation unit is advantageously placed downstream of the zone for recovering said first fraction to obtain a hydrocarbon fraction the propylene content of which is enhanced. Said second fraction is constituted by hydrogen, present in a proportion representing at least 7% by weight of said second fraction, which also advantageously contains at least 60% by weight of ethylene which may be isolated from said second fraction to be upgraded as a petrochemicals intermediate. Said second fraction is advantageously recycled upstream of said reaction unit to increase the quantity of propylene formed. At least part of said third fraction, comprising non aromatic hydrocarbon compounds containing 4, 5 and/or 6 carbon atoms per molecule, is advantageously recycled upstream of said reaction unit when this is operating as a moving bed. It contains unreacted olefinic compounds. It also contains inert paraffins which, when recycled to the inlet to the reaction zone, can increase the selectivity of the catalyst towards propylene by reducing the olefin partial pressure. Preferably, the proportion of said third fraction which is recycled is such that the ratio (mass flow rate of the third fraction at the inlet to said reaction zone/mass flow rate of fresh hydrocarbon feed entering said reaction zone before mixing with the recycled fractions), termed the recycle, is in the range 0.5 to 2, preferably in the range 0.5 to 1.5. Recycling at least a portion of said third fraction can at least partially, preferably in its entirety, allow the unconverted olefins to be re-introduced into said reaction unit as well as unwanted secondary products formed during the conversion reaction which can be converted into propylene. A high recycle rate causes a high consumption of energy and is thus prejudicial to the viability of the process, even more so when the recycle is high, namely more than 1.5, preferably more than 2, and the general result is a low activity catalyst.

The catalyst used in each of the reactors of the reaction unit of the process of the invention is in the form of spherical beads with a double porosity measured by mercury porosimetry: a macroporosity characterized by a macroporous mercury volume in a range of 0.10 to 0.20 ml/g and preferably in a range of 0.12 to 0.18 ml/g, and a mesoporosity characterized by a mesoporous mercury volume in a range of 0.25 to 0.35 ml/g, preferably in a range of 0.28 to 0.35 ml/g. The macroporosity is also characterized by the presence of macroporous regions of more than 50 nm, preferably more than 100 nm, and/or results in a textural intraparticulate macroporosity; the mesoporosity is also characterized by the presence of mesoporous domains in a range of 7 to 50 nm, preferably in a range of 8 to 10 nm. The proportion of the pore volume of said beads with a pore size of less than 20 nm is in the range 60% to 70%.

Mercury porosimetry analysis corresponds to intrusion of a volume of mercury which is characteristic of the existence of mesopores and macropores into said catalyst in accordance with US standard ASTM D4284-83 at a maximum pressure of 4000 bars, using a surface tension of 484 dynes/cm and a contact angle of 140° (value selected following the recommendations in the work "Technique de l'ingénieur, traité analyse et caractérisation", page 1050, by J Charpin and B Rasneur), the pores being assumed to be cylindrical in shape. This technique can produce the mesoporous mercury volume, defined as the volume of mercury adsorbed by all pores with a diameter in the mesopore range, namely in the range 3.6 to 50 nm. Similarly, the mesoporous mercury volume is defined as being the volume of mercury adsorbed by all pores with a diameter of more than 50 nm.

In accordance with the invention, the zeolite present in each of said spherical beads forming the catalyst is preferably selected from zeolites with structure type MEL, MFI, NES, EUO, FER, CHA, MFS, MWW and NES and highly preferably, it is a zeolite with structure type MFI, in particular ZSM-5 zeolite. Said zeolite may also advantageously be selected from NU-85, NU-86 and IM-5 zeolites. Advantageously, said zeolite in each of said spherical beads forming the catalyst has a Si/Al ratio in the range 50 to 500, highly advantageously in the range 70 to 140. Said zeolite is dispersed in a alumina-based support in each of said spherical beads forming the catalyst. The proportion of zeolite in each of said beads forming the catalyst is in the range 15% to 90% by weight, preferably in the range 30% to 80% by weight and more preferably in the range 35% to 50% by weight, the remainder being constituted by the alumina-based support.

According to the invention, said spherical beads constituting said catalyst used in the process of the invention have a diameter in the range 1 to 3 mm, preferably in the range 1.8 to 2.2 mm. The morphology and size distribution of the beads are established by analyzing photos obtained by scanning electron microscopy (SEM). The catalyst has a specific surface area $S_{BET}$ in the range 290 to 350 m$^2$/g. It has a strength, measured as the crush strength using the ASTM D4179-88a method, such that the CS is at least 10 N and preferably at least 20 N.

The catalyst is prepared using a process comprising a) preparing at least one emulsion formed from at least one porogen, water and a surfactant, b) preparing a suspension formed from water, acid, a source of alumina, at least one zeolite and said emulsion prepared during step a), c) forming by drop coagulation, consisting of i) passing said suspension formed in b) into a draining pot constituted by nozzles each having an orifice calibrated to form droplets, ii) passing, in a downward movement, said droplets into a column containing an upper phase constituted by an organic phase and a lower phase constituted by a basic aqueous phase, the organic phase-aqueous phase interface being constituted by a surfactant, to harvest spherical beads, d) drying said beads and e) calcining said beads.

To prepare the emulsion of step a), the porogen used to form the pores in the final catalyst beads is an oil cut, preferably a paraffinic kerosene cut containing 10 to 14 carbon atoms, formed from normal and iso paraffins, and with a boiling point in the range 220° C. to 350° C. Advantageously, the porogen used is a commercial compound, isane®, the composition of which includes several aromatic components. The surfactant used to prepare the emulsion is a non-ionic emulsifying agent. It is selected to ensure the stability of the emulsion. It is essential that it can be eliminated by combustion and that it is liquid at ambient temperature. In general, the surfactant selected is a commercial compound, Galoryl® sold by Comptoir Franqais des Produits Industriels. The mixture of water, porogen and surfactant is produced at ambient temperature for a period which is preferably in the range 10 to 15 minutes.

In a first step, preparation of the suspension in step b) consists of mixing the water, acid and the alumina source then introducing at least one zeolite into the mixture formed and finally introducing the emulsion formed during step a). The water, acid and alumina source are mixed at ambient temperature. The water and acid are mixed simultaneously, then the alumina source is introduced. The acid used to prepare the suspension is advantageously selected from strong acids, preferably nitric acid and sulphuric acid. Highly advantageously, nitric acid is used, in particular 59.68% by weight nitric acid. Preferably, a mixture of nitric acid and phosphoric acid is used. The alumina source, used to prepare the suspension, is preferably selected from the group formed by hydragillite, bayerite, pseudoboehmite, amorphous gels, transition aluminas which comprise at least one phase taken from the group comprising rho, chi, eta, gamma, kappa, theta and alpha phases. More preferably, said alumina source is a pseudoboehmite, for example PURAL SB3® sold by SASOL. Preparation of the suspension is continued by introducing at least one zeolite, in powder form, into the mixture containing the water, acid and source of alumina, at ambient temperature. The zeolite used to prepare the suspension may either be in the as-synthesized form, or in the exchanged form or in the calcined form (hydrogen form). Preparation of the Suspension is Terminated by Introducing the Emulsion Prepared During Step a) into the mixture (water, acid, alumina source, zeolite). Said suspension is stirred vigorously until the viscosity of said suspension is in the range 250 to 400 MPa·s. The vigorous stirring is preferably carried out at between 1100 and 1900 rpm, more preferably between 1400 and 1700 rpm for about ten minutes, generally between 10 and 15 minutes, then the rate is reduced so that it is preferably in the range 550 to 700 rpm until the viscosity of said suspension is in the range 250 to 400 MPa·s. Thus, the suspension has rheological properties which are suitable for flowing through the nozzles of the draining pot used in step c) for forming the catalyst by drop coagulation. The viscosity of said suspension is measured using a plane/plane rheometer at a shear rate gradient of 100 $s^{-1}$. The viscosity which is measured is the relative viscosity.

The stirring rates are those obtained using an ER550 agitator from Euromélanges. The motor operates with direct single phase current of 220 volts; the power is 0.55 kW at 3000 rpm.

Depending on the catalyst preparation process used in the conversion process of the invention, the quantities of the various reagents present in the emulsion and in the suspension are such that:

- the amount of porogen, equal to the mass of porogen over the mass of water engaged in the emulsion and the water engaged in the suspension, is in the range 1.5% to 8% by weight, preferably in the range 2% to 7.5% by weight. The water present in the compounds engaged in the emulsion and suspension, in particular the alumina source and the zeolite, are ignored for the purposes of calculating the amount of porogen;
- the proportion of surfactant present in the emulsion is calculated as the mass of surfactant over the mass of porogen, and is in the range 1% to 10% by weight, preferably in the range 4% to 8% by weight and more preferably in the range 5% to 7% by weight, with 7 being exclude from the range 5-7;
- the proportion of water present in the suspension (after introducing the emulsion into the suspension) is such that the dry mass ratio (corresponding to the mass of powder, namely the alumina source and the zeolite, dehydrated) to the total mass of water is in the range 20% to 30% by weight, preferably in the range 24% to 28% by weight;
- the quantity of water engaged in the emulsion represents 9% to 11% by weight of the total quantity of water engaged in the suspension;
- the amount of acid engaged in the suspension, equal to the product of the concentration (% by weight) of said acid by the mass of said acid with respect to the dry mass of the alumina source, is in the range 10% to 15% by weight;
- the proportion of zeolite present in the suspension, calculated as the ratio of the dry mass of the zeolite to the dry mass of the alumina source and the zeolite, is in the range 10% to 55% by weight, preferably in the range 30% to 55% by weight and more preferably in the range 35% to 50% by weight;
- the proportion of phosphoric acid, advantageously introduced with the nitric acid, is such that the weight ratio of $P_2O_5$/dry alumina source is in the range 1% to 5% by weight.

The dry mass of the alumina source and that of the zeolite are accessible by measuring the loss on ignition (LOI) of each of these powders.

Drop coagulation forming consists, during a first step i), of passing said suspension prepared during step b) into a draining pot constituted by nozzles, each of said nozzles having an orifice which is calibrated to form droplets. Said draining pot is placed at the head of a column containing an upper phase constituted by an organic phase and a lower phase constituted by a basic aqueous phase, the organic phase-aqueous phase interface being constituted by a surfactant. Said nozzles each have an orifice with a calibrated size to form droplets with a diameter in the range about 2 to 3 mm. The dimension of the droplets obtained depends not only on the internal diameter of the nozzles (wetting phenomenon), which is generally about 1 mm, but also on the circular cross section of said nozzles at their ends. In step ii) of the drop coagulation method, the droplets ii) containing an upper phase constituted by an organic phase and a lower phase constituted by an aqueous phase, the organic phase-aqueous phase interface being constituted by a surfactant in order to harvest spherical beads with a diameter in the range about 2 to 3 mm. Said organic phase is selected so that it has a density which is slightly lower than that of water. Preferably, the organic phase is selected so that the density is in the range 0.7 to 0.9 kg/$m^3$ at 15° C. Said organic phase is selected in a manner such that the surface tension between said organic phase and said aqueous basic phase is high, generally in the range $60 \times 10^{-3}$ to $80 \times 10^{-3}$ N/m. Advantageously, an oil cut, preferably a paraffinic kerosene cut, in particular isane®, is selected as the organic phase. The surfactant separates the organic and aqueous phases and is preferably a cationic SF. Preferably, ammonyl BR 1244® is used, which is an alkyl dimethylbenzylammonium bromide in aqueous solution sold by SEPIC SA. The basic aqueous phase constituting the lower portion of the column is advantageously a basic solution having an ammonium concentration in the range 25 to 33 g/l, preferably in the range 27 to 29 g/l. Said basic aqueous solution has a pH in the range 8 to 10.

The column used for drop coagulation is prepared by first introducing said organic phase, preferably isane®, followed by said basic aqueous solution, preferably said ammoniacal solution and finally said surfactant, preferably ammonyl BR 1244. Said surfactant may either be introduced directly into said basic aqueous solution or introduced into said column by continuous injection. The volume of said column is constituted by said surfactant by up to 1% by volume, up to 4% by volume of air, 6% to 10% by volume of said organic phase, the remainder being occupied by said basic aqueous phase.

The fall rate of droplets in the column is such that they conserve their spherical shape to obtain spherical beads with a diameter in the range 1 to 3 mm, preferably 1.8 to 2.2 mm. The droplets, which are subjected to van der Waals forces on passing through said aqueous solution, stiffen and aggregate. This results in the formation of beads at the outlet from said column. Said beads are then entrained by a stream of said basic aqueous phase, preferably by an ammoniacal stream, recovered and separated from said aqueous phase on a sieve. The ammoniacal aqueous phase recovered is advantageously recycled to said column which is used for the drop coagulation.

In step d) of the process for preparing the catalyst used in the conversion process of the invention, said beads are dried in a ventilated cabinet at ambient temperature then oven dried at a temperature in the range 60° C. to 120° C. Drying in the cabinet and drying each generally lasts 10 to 20 hours.

In step e) of the process for preparing the catalyst used in the conversion process of the invention, the beads are then calcined at a temperature in the range 500° C. to 800° C., preferably in the range 550° C. to 700° C. Calcining generally lasts several hours, preferably 3 to 5 hours.

The reaction unit provided with said catalyst in the form of spherical beads for carrying out the process of the invention functions either in moving bed or in fixed bed mode. When it functions in fixed bed or moving bed mode, the catalyst is periodically regenerated and said unit alternately carries out the reaction for producing propylene and that for regenerating said catalyst to eliminate coke deposited on its surface during the reaction. The regeneration phase also generally comprises a phase for combustion of carbonaceous deposits formed on the catalyst, for example using an air/nitrogen mixture or air depleted in oxygen (in particular by recirculating fumes) or simply air, said combustion phase generally using a temperature in the range 400° C. to 650° C., the pressure usually being close to the pressure used in the reaction unit. Said combustion phase is followed by calcining in dry air, optionally diluted with nitrogen, at a temperature in the range 500° C. to 600° C.

The invention will be better understood from the following description of an implementation which is given by way of illustration; the present invention is not limited to this implementation alone.

BRIEF DESCRIPTION OF DRAWINGS

The attached drawing is a schematic flowsheet of such an implementation of the invention.

DETAILED DESCRIPTION OF DRAWING

Figure 1:
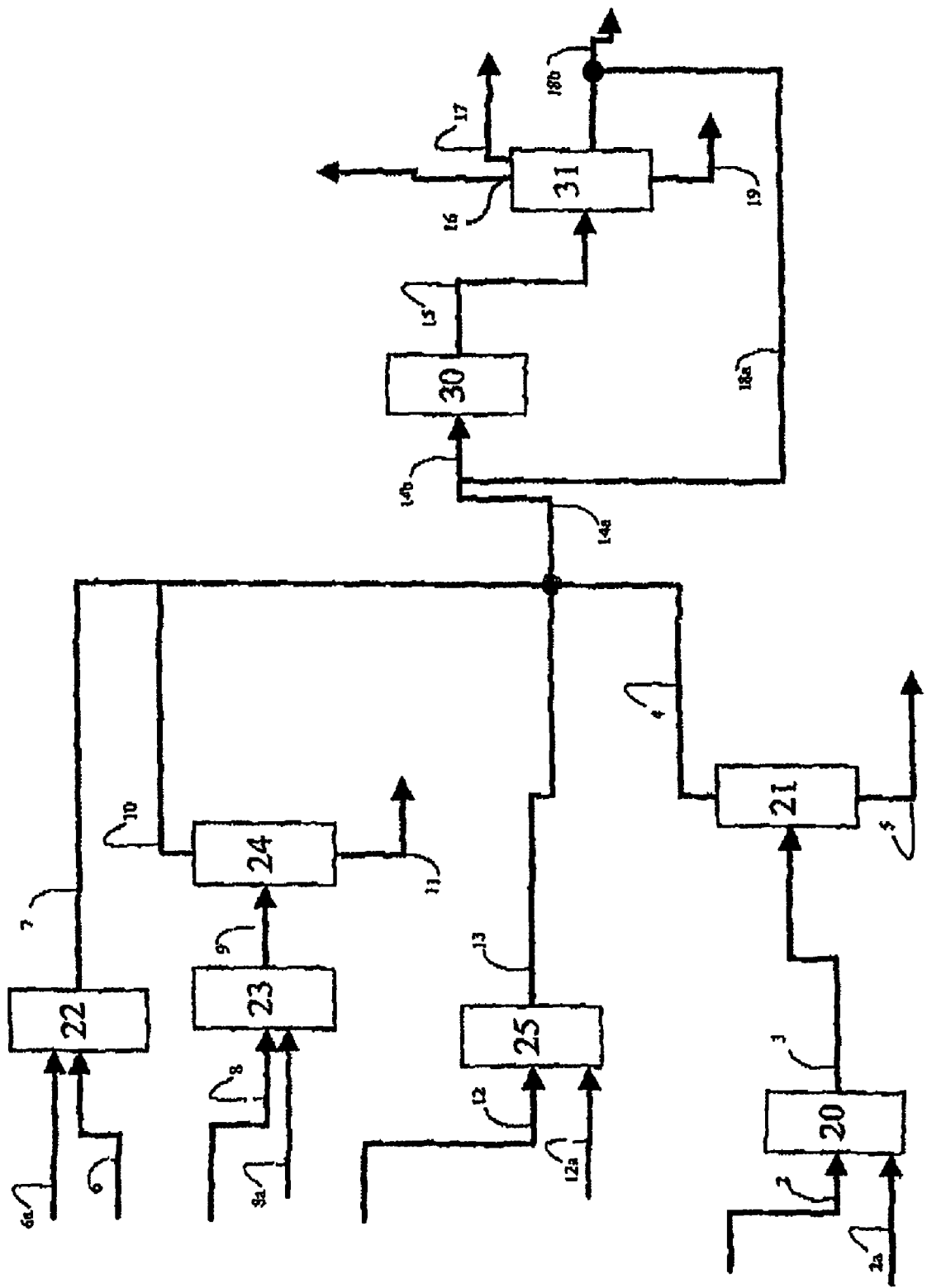

An olefinic C4 cut from a steam cracking unit as defined above is fed via a line 6 to a unit for selective hydrogenation of poly-unsaturated compounds 22 where hydrogen has also been introduced via a line 6a. Said selective hydrogenation unit is operated under conditions such that the effluent 7 resulting from conversion of the poly-unsaturated compounds into mono-olefinic compounds in the unit 22 has a poly-unsaturated compounds content in the range 10 ppm to 4000 ppm, preferably between 50 ppm and 1000 ppm.

An olefinic gasoline cut as defined above from a steam cracking unit is fed via a line 8 to a unit for selective hydrogenation of poly-unsaturated compounds 23 where hydrogen has also been introduced via a line 8a. The effluent 9 leaving said unit 23 is introduced into a distillation unit 24 which carries out separation of a light fraction 10 and a heavy fraction 11. Said light fraction is essentially, i.e. 10% to 40% by weight of the initial gasoline cut, formed by compounds containing 5 carbon atoms wherein at least 60% by weight is C5 mono-olefins (pentene and isopentene). The heavy fraction 11 is formed by aromatic compounds (benzene, toluene, xylene, ethylbenzene), olefins (C6 olefins) and cyclo-olefins (dihydro-dicyclopentadiene and alkylated derivatives).

A gasoline cut from FCC as defined in the description above is fed via a line 2 to a unit for selective hydrogenation of poly-unsaturated compounds 20 into which hydrogen has also been introduced via a line 2a. The effluent 3 leaving said unit 20 is introduced into a separation unit 21 which can extract a light fraction 4 mainly comprising hydrocarbon compounds containing 5 carbon atoms, in particular C5 mono-olefins, namely pentene and isopentene. A heavy fraction 5 formed of paraffinic, olefinic and aromatic compounds (benzene, toluene, xylene, ethylbenzene) is also extracted from the tail of the unit 21.

A C4 cut from FCC as defined in the description above is fed via a line 12 to a unit for selective hydrogenation of poly-unsaturated compounds 25 into which hydrogen has also been introduced via a line 12a. Cut 12 may advantageously be free from reactive sulphur containing species continued therein before being introduced into said selective hydrogenation unit 25. The effluent 13 from the unit 25 contains C4 olefins (2-butene, isobutene, 1-butene) and C4 paraffins (isobutane, butane).

Effluents 7, 10, 13 and 4 are mixed upstream of a reaction unit 30 to form the feed 14a to be converted into propylene. Said feed is introduced into the reaction unit 30 provided with at least one catalyst, said unit functioning in moving bed mode. The effluent leaving said unit 30 is introduced into a separation unit 31 from which four distinct streams are harvested. The overhead stream 16 is rich in hydrogen and also contains ethylene. Stream 17 contains the desired product, propylene. The olefins which are not converted in said unit 30 and secondary products formed in said unit 30 form a stream 18 which is recycled in part upstream of said unit 30 via line 18a, while the stream 18b containing mainly C4 and/or C5 paraffins constitutes the purge. The complete feed, integrating the recycled stream 18a upstream of said unit 30, is constituted by the stream 14b.

The following examples illustrate the invention.

EXAMPLE 1 (INVENTION)

Preparation of catalyst C1 with a Porogen Content of 2.0% by Weight

An emulsion was prepared by introducing 244 g of water, 49 g of porogen constituted by isane and 2.9 g of surfactant constituted by galoryl into a one litre beaker. The mixture was stirred at 500 rpm for 15 minutes.

A suspension was prepared by introducing 2198 g of permutated water and 69 g of 59.68% by weight nitric acid into a 4 litre beaker, the mixture being stirred at 400 rpm for 5 min. 450 g of PURAL SB3 (loss on ignition=26.10%) was then added and the mixture (permutated water, nitric acid and PURAL SB3) was stirred at 1600 rpm for 14 minutes. 332 g of ZSM-5 zeolite in the H form with a Si/Al ratio of 140, sold by Zeolyst, was then added to the mixture (permutated water, nitric acid and PURAL SB3); the resulting mixture was stirred at 1600 rpm for 3 minutes then the emulsion formed from the water, the isane and the galoryl was added to said mixture. This was all stirred at 1600 rpm for 13 minutes then the stirring rate was reduced to 625 rpm for 70 minutes. The viscosity of said mixture was then measured using a plane/plane rheometer at a shear gradient of 100 s$^{-1}$ and was equal to 270 MPa·s.

For drop coagulation, a 9.4 litre glass column was used. Said column was charged with 7 litres of an ammoniacal solution with a concentration of 28 g/l, 0.4 litres of a solution of 1% by weight ammonyl and 0.7 litres of isane. The column was topped by a draining pot constituted by nozzles, each being provided with a circular orifice with a diameter of 1 mm. The suspension was introduced into said draining pot, the draining rate being such that 80 droplets issued from the nozzle per minute. The droplets then fell into the isane phase then into the 28 g/l ammoniacal phase, the isane phase-ammoniacal phase interface being constituted by ammonyl. The beads obtained were placed in a ventilated cabinet at ambient temperature overnight to carry out a first mild drying then placed in an oven overnight at 100° C. The dried beads were calcined for 2 hours in a muffle furnace at 600° C. Catalyst C1 was obtained the textural and mechanical characteristics of which are shown in Table 1. It had a mechanical strength, given by the crush strength (CS), of 26 N.

EXAMPLE 2 (INVENTION)

Preparation of Catalyst C2 with a Porogen Content of 4.0% by Weight

An emulsion was prepared by introducing 247 g of water, 99 g of porogen constituted by isane and 5.9 g of surfactant constituted by galoryl into a one litre beaker. The mixture was stirred at 500 rpm for 15 minutes.

A suspension was prepared by introducing 2219 g of permutated water and 73 g of 59.68% by weight nitric acid into a 4 litre beaker, the mixture being stirred at 400 rpm for 5 min. 450 g of PURAL SB3 (loss on ignition=26.10%) was then added and the mixture (permutated water, nitric acid and PURAL SB3) was stirred at 1600 rpm for 14 minutes. 343 g of ZSM-5 zeolite in the H form with a Si/Al ratio of 140, sold by Zeolyst, was then added to the mixture (permutated water, nitric acid and PURAL SB3); the resulting mixture was stirred at 1600 rpm for 3 minutes then the emulsion formed from the water, the isane and the galoryl was added to said mixture. This was all stirred at 1600 rpm for 13 minutes then the stirring rate was reduced to 625 rpm for 70 minutes. The viscosity of said mixture was then measured using a plane/plane rheometer at a shear gradient of 100 $s^{-1}$ and was equal to 320 MPa·s.

For drop coagulation, a 9.4 litre glass column was used. Said column was charged with 7 litres of an ammoniacal solution with a concentration of 28 g/l, 0.4 litres of a solution of 1% by weight ammonyl and 0.7 litres of isane. The column was topped by a draining pot constituted by nozzles, each being provided with a circular orifice with a diameter of 1 mm. The suspension was introduced into said draining pot, the draining rate being such that 80 droplets issued from the nozzle per minute. The droplets then fell into the isane phase then into the 28 g/l ammoniacal phase, the isane phase-ammoniacal phase interface being constituted by ammonyl. The beads obtained were placed in a ventilated cabinet at ambient temperature overnight to carry out a first mild drying then placed in an oven overnight at 100° C. The dried beads were calcined for 2 hours in a muffle furnace at 600° C. Catalyst C2 was obtained the textural and mechanical characteristics of which are shown in Table 1. It had a mechanical strength, given by the crush strength (CS), of 16 N.

EXAMPLE 3 (INVENTION)

Preparation of Catalyst C3 with a Porogen Content of 7.5% by Weight

An emulsion was prepared by introducing 249 g of water, 187 g of porogen constituted by isane and 11.2 g of surfactant constituted by galoryl into a one litre beaker. The mixture was stirred at 500 rpm for 15 minutes.

A suspension was prepared by introducing 2243 g of permutated water and 68 g of 59.68% by weight nitric acid into a 4 litre beaker, the mixture being stirred at 400 rpm for 5 min. 450 g of PURAL SB3 (loss on ignition=26.10%) was then added and the mixture (permutated water, nitric acid and PURAL SB3) was stirred at 1600 rpm for 14 minutes. 339 g of ZSM-5 zeolite in the H form with a Si/Al ratio of 140, sold by Zeolyst, was then added to the mixture (permutated water, nitric acid and PURAL SB3); the resulting mixture was stirred at 1600 rpm for 3 minutes then the emulsion formed from the water, the isane and the galoryl was added to said mixture. This was all stirred at 1600 rpm for 13 minutes then the stirring rate was reduced to 625 rpm for 70 minutes. The viscosity of said mixture was then measured using a plane/plane rheometer at a shear gradient of 100 s1 and was equal to 270 MPa·s.

For drop coagulation, a 9.4 litre glass column was used. Said column was charged with 7 litres of an ammoniacal solution with a concentration of 28 g/l, 0.4 litres of a solution of 1% by weight ammonyl and 0.7 litres of isane. The column was topped by a draining pot constituted by nozzles, each being provided with a circular orifice with a diameter of 1 mm. The suspension was introduced into said draining pot, the draining rate being such that 80 droplets issued from the nozzle per minute. The droplets then fell into the isane phase then into the 28 g/l ammoniacal phase, the isane phase-ammoniacal phase interface being constituted by ammonyl. The beads obtained were placed in a ventilated cabinet at ambient temperature overnight to carry out a first mild drying then placed in an oven overnight at 100° C. The dried beads were calcined for 2 hours in a muffle furnace at 600° C. Catalyst C3 was obtained the textural and mechanical characteristics of which are shown in Table 1. It had a mechanical strength, given by the crush strength (CS), of 26 N.

EXAMPLE 4 (COMPARATIVE)

Preparation of Catalyst C0 with no Porogen

A suspension was prepared by introducing 2292 g of permutated water and 68 g of 59.76% by weight nitric acid into a 4 litre beaker, the mixture being stirred at 400 rpm for 5 min. 450 g of PURAL SB3 (loss on ignition=26.10%) was then added and the mixture (permutated water, nitric acid and PURAL SB3) was stirred at 1600 rpm for 14 minutes. 339 g of ZSM-5 zeolite in the H form with a Si/Al ratio of 140, sold by Zeolyst, was then added to the mixture (permutated water, nitric acid and PURAL SB3); the resulting mixture was stirred at 1600 rpm for 16 minutes then the stirring rate was reduced to 625 rpm for 70 minutes. The viscosity of said mixture was then measured using a plane/plane rheometer at a shear gradient of 100 $s^{-1}$ and was equal to 270 MPa·s.

For drop coagulation, a 9.4 litre glass column was used. Said column was charged with 7 litres of an ammoniacal solution with a concentration of 28 g/l, 0.4 litres of a solution of 1% by weight ammonyl and 0.7 litres of isane. The column was topped by a draining pot constituted by nozzles, each being provided with a circular orifice with a diameter of 1 mm. The suspension was introduced into said draining pot, the draining rate being such that 80 droplets issued from the nozzle per minute. The droplets then fell into the isane phase then into the 28 g/l ammoniacal phase, the isane phase-ammoniacal phase interface being constituted by ammonyl. The beads obtained were placed in a ventilated cabinet at ambient temperature overnight to carry out a first mild drying then placed in an oven overnight at 100° C. The dried beads were calcined for 2 hours in a muffle furnace at 600° C. Catalyst C0 was obtained, not in accordance with the invention; its textural and mechanical characteristics are shown in Table 1.

The textural and mechanical characteristics of catalysts C0, C1, C2 and C3 are shown in Table 1 below.

TABLE 1

Textural and mechanical characteristics of catalysts C0, C1, C2 and C3

|  | C0 | C1 | C2 | C3 |
|---|---|---|---|---|
| BET specific surface area ($m^2/g$) | 326 | 321 | 329 | 323 |
| Hg pore volume (ml/g) | 0.30 | 0.41 | 0.47 | 0.49 |
| Macroporous Hg vol (ml/g) | 0.005 | 0.12 | 0.18 | 0.14 |
| Mesoporous Hg vol (ml/g) | 0.29 | 0.29 | 0.29 | 0.35 |
| Spherical bead size (mm) | 1.8-2.2 | 1.8-2.2 | 1.8-2.2 | 1.8-2.2 |

EXAMPLE 5

Catalytic Performance of Catalysts C0, C1, C2 and C3 in a Process for Producing Propylene from a Feed Constituted by 1-Butene and 1-Pentene Each of catalysts C0, C1, C2 and C3 was tested separately in a propylene production process provided with a unit having a reactor supplied with 1.5 g of one of said catalysts placed in a bed of SiC with the same granulometry. The reactor was heated to 510° C. The feed supplying said unit was composed of 50% by weight of pure 99% molar 1-butene and 50% by weight of 1-pentene. The flow rate of said feed was 6.75 g/h for catalysts C1, C2 and C3. Nitrogen was also introduced into said unit at a flow rate of 6.7 l/h. Said unit operated in fixed bed mode. The reaction in said unit was carried out at a pressure of 0.05 MPa. The HSV was 4.5 $h^{-1}$ when catalysts C1, C2 and C3 were tested and was 3 $h^{-1}$ when catalyst C0 was tested and for which the flow rate was 4.5 g/h.

Gas was harvested from the outlet from the reaction unit and analyzed by gas chromatography.

The catalytic performance obtained for each of catalysts C0, C1, C2 and C3 during the tests described above are given in Table 2.

TABLE 2

Catalytic performance obtained with each of catalysts C0, C1, C2 and C3

|  | C0 | C1 | C2 | C3 |
|---|---|---|---|---|
| HSV ($h^{-1}$) | 3 | 4.5 | 4.5 | 4.5 |
| Time under flow (h) | 10 | 10 | 10 | 10 |
| Olefins conversion (%) | 70.5 | 70.2 | 70.7 | 70.1 |
| Propylene selectivity (%) | 31.5 | 39.6 | 39.3 | 41.6 |
| Propylene yield (%) | 22.2 | 27.8 | 27.8 | 29.1 |
| Propylene/isobutene | 2.1 | 2.4 | 2.3 | 2.5 |

TABLE 2-continued

Catalytic performance obtained with each of catalysts C0, C1, C2 and C3

|  | C0 | C1 | C2 | C3 |
|---|---|---|---|---|
| Time under flow (h) | 40 | 40 | 40 | 40 |
| Olefins conversion (%) | 64.1 | 64.2 | 64.1 | 66.8 |
| Propylene selectivity (%) | 36.4 | 43.1 | 42.4 | 42.5 |
| Propylene yield (%) | 23.3 | 27.7 | 27.2 | 28.4 |
| Propylene/isobutene | 1.7 | 2.0 | 2.0 | 2.2 |

The olefin conversion corresponds to the quantity by weight of C4/C5 olefins at the outlet subtracted from the quantity by weight of C4/C5 olefins at the inlet to the reaction zone, divided by the quantity by weight of C4/C5 olefins at the inlet. The propylene yield is calculated as the quantity by weight of propylene produced with respect to the quantity of fresh feed.

The results shown in Table 2 show that at olefin iso-conversion (HSV=4.5 $h^{-1}$ for C1, C2 and C3 and HSV=3 $h^{-1}$ for C0), catalysts C1, C2 and C3 were more selective for the desired product, propylene, and resulted in a better propylene yield than catalyst C0 which was prepared in the absence of porogen.

The tests were carried out for a period of 10 hours and 40 hours after starting injection of the feed (time under flow). Despite the deactivation observed for each of the catalysts as the time under flow rose (drop in conversion for all catalysts between the tests after 10 h feed injection and the tests after 40 h feed injection), the propylene selectivity and as a result the propylene/isobutene ratio were always better when catalysts C1, C2 and C3 were used than when catalyst C0 was used.

EXAMPLE 6

Catalytic Performance of Catalysts C0, C1, C2 and C3 in a Propylene Production Process Using a Feed Combining a Feed Derived from a Steam Cracking Unit and a Feed Derived from FCC Each of catalysts C0, C1, C2 and C3 was tested separately in a propylene production process provided with a unit supplied with a reactor having one of said catalysts. Each catalyst used in said process was supplied with a feed which had been heated to 510° C. before being introduced into the reactor; the composition is given in Table 3 (see the composition of streams 6, 12, 2 and 8 which correspond to the streams shown in FIG. 1). The flow rate of each of the streams is given in kg/h in Table 3. Said unit operated in moving bed mode. The reaction in said unit was carried out at a pressure of 0.15 MPa. The HSV was 4.5 $h^{-1}$. Streams 14a and 18a shown in Table 3 correspond to the numbering of the streams shown in FIG. 1.

Gas was harvested from the outlet from the reaction unit and analyzed by gas chromatography.

TABLE 3

Composition of various hydrocarbon streams passing through the propylene production process in the presence of catalysts C0, C1, C2 and C3.

| | Stream | | | | | | | | |
|---|---|---|---|---|---|---|---|---|---|
|  | 6 | 12 | 2 | 8 | 14a | 18a | 18a | 18a | 18a |
| Catalyst |  |  |  |  |  | C0 | C1 | C2 | C3 |
| n-C4 = | 2340 | 3556 |  |  | 9672 | 11788 | 5402 | 5346 | 4413 |
| iC4 = | 2889 | 1524 |  |  | 4413 | 6061 | 3473 | 3409 | 2897 |

TABLE 3-continued

Composition of various hydrocarbon streams passing through the propylene production process in the presence of catalysts C0, C1, C2 and C3.

| | Stream | | | | | | | | |
|---|---|---|---|---|---|---|---|---|---|
| | 6 | 12 | 2 | 8 | 14a | 18a | 18a | 18a | 18a |
| C4 == | 3976 | 20 | | | 22 | 87 | 43 | 40 | 35 |
| C4P | 795 | 4900 | | | 5893 | 30321 | 15161 | 13834 | 12314 |
| n + i C5 = | | | 6000 | 6500 | 12500 | 3654 | 2549 | 2497 | 2216 |
| cycloC5 | | | 500 | 2500 | 3000 | 90 | 74 | 74 | 75 |
| C5 == | | | | | | | | | |
| C5P | | | 3500 | 1000 | 4500 | 20046 | 10087 | 9211 | 8140 |
| C6-C12 | | | 50000 | 30000 | | 10487 | 8740 | 8652 | 8099 |
| Total (kg/h) | 10000 | 10000 | 60000 | 40000 | 40000 | 82533 | 45530 | 43062 | 38188 | in which:
nC4 = is n-butene,
iC4 = is isobutene,
C4 == is butadiene,
C4P are C4 paraffins,
n + i C5 = are n- and isopentenes,
cycloC5 is cyclopentene,
C5 == is pentadiene,
C5P are C5 paraffins and cyclopentane,
C6-C12 are hydrocarbons (paraffins, olefins, aromatics) containing 6 to 12 carbon atoms per molecule.

The tests were carried out for a cycle time of 48 hours, the cycle time corresponding to the time during which the catalyst was in contact with the feed to conduct the propylene production reaction. After this 48 hour period, each catalyst was regenerated.

The catalytic performance obtained by each of catalysts C0, C1, C2 and C3 during the tests described above are given in Table 4.

TABLE 4

Catalytic performance obtained by each of catalysts C0, C1, C2 and C3

| | Catalyst | | | |
|---|---|---|---|---|
| | C0 | C1 | C2 | C3 |
| Olefin conversion (%) | 79.2 | 77.5 | 75.3 | 76.3 |
| Propylene selectivity (%) | 39.0 | 39.9 | 41.0 | 40.5 |
| Propylene yield (%) | 30.9 | 30.9 | 30.9 | 30.9 |
| Recycle ratio | 2.1 | 1.1 | 1.1 | 1.0 |

The olefin conversion corresponds to the quantity by weight of C4/C5 olefins at the outlet subtracted from the quantity by weight of C4/C5 olefins at the inlet to the reaction zone before the stream recycle 18a, divided by the quantity by weight of C4/C5 olefins at the inlet. The propylene yield is calculated as the quantity by weight of propylene produced with respect to the quantity of fresh feed.

The results shown in Table 4 show that the processes carried out in the presence of catalysts C1, C2 and C3 result in a propylene yield which is identical to that obtained by the process carried out using catalyst C0 while the flow rate of the recycled stream (18a) is half that used to carry out the process using catalyst C0. Halving the recycle ratio when the catalyst used in the propylene production process is prepared in the presence of a porogen can substantially reduce the overall energy consumption of processes carried out in the presence of catalysts C1, C2 and C3. Further, the selectivity towards propylene is increased when the catalysts are prepared in the presence of a porogen.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 06/07494, filed Aug. 24, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for once-through conversion of a hydrocarbon feed comprising at least olefins containing 4 carbon atoms and at least olefins containing 5 carbon atoms, producing propylene, said process comprising passing said feed into at least one reaction unit provided with at least one catalyst in the form of spherical beads with a diameter in the range 1 to 3 mm, each of said spherical beads comprising at least one zeolite and at least one alumina-based, support and having a pore distribution such that the macroporous volume, measured by mercury porosimetry, is in the range 0.10 to 0.20 ml/g and the mesoporous volume, measured by mercury porosimetry, is in the range 0.25 to 0.35 ml/g, said catalyst further having a proportion of pore volume with pore size less than 20 nm in the range of 60-70%.

2. A once-through conversion process according to claim 1, in which each of said spherical beads has macroporous domains of more than 50 nm.

3. A once-through conversion process according to claim 1, in which said catalyst is in the form of spherical beads with a diameter in the range 1.8 to 2.2 mm.

4. A once-through conversion process according to claim 1, in which said zeolite present in each of said spherical beads is selected from zeolites with structure type MEL, MFI, NES, EUO, FER, CHA, MFS, MWW and NES.

5. A once-through conversion process according to claim 4, in which said zeolite is a zeolite with structure type MFI.

6. A once-through conversion process according to claim 1, in which said catalyst is prepared using a process comprising a) preparing at least one emulsion formed from at least one porogen, water and a surfactant, b) preparing a suspension formed from water, acid, a source of alumina, at least one zeolite and said emulsion prepared during step a), c) forming by drop coagulation, consisting of i) passing said suspension formed in b) into a draining pot constituted by nozzles each having an orifice calibrated to form droplets, ii) passing, in a downward movement, said droplets into a column containing an upper phase constituted by an organic phase and a lower phase constituted by a basic aqueous phase, the organic phase-aqueous phase interface being constituted by a surfactant, to harvest spherical beads, d) drying said beads and e) calcining said beads.

7. A once-through conversion process according to claim 6, in which said porogen, used to prepare the emulsion in said step a), is a paraffinic kerosene cut containing 10 to 14 carbon atoms, formed from normal and isoparaffins, and having a boiling point in the range 220° C. to 350° C.

8. A once-through conversion process according to claim 6, in which the porogen content, equal to the mass of porogen over the mass of water engaged in the emulsion and the water engaged in the suspension, is in the range 1.5% to 8% by weight.

9. A once-through conversion process according to claim 6, in which the amount of acid engaged in the suspension is equal to the product of the concentration (% by weight) of said acid and the mass of said acid with respect to the dry mass of the alumina source, is in the range 10% to 15% by weight.

10. A once-through conversion process according to claim 1, in which said hydrocarbon feed derives either from the C4/C5 olefinic cut from the steam cracking unit or from olefinic C4 cuts and gasoline derived from a fluid catalytic cracking (FCC) unit or from a mixture of said cuts derived from steam cracking and fluid catalytic cracking.

11. A once-through conversion process according to claim 1, in which said reaction unit carrying out the conversion of said hydrocarbon feed for the production of propylene and provided with at least one said catalyst is carried out at a temperature in the range 450° C. to 580° C., at an operating pressure in the range 0.01 to 0.5MPa and at an HSV in the range 1 to 20 h$^{-1}$.

12. A once-through conversion process according to claim 1, in which said catalyst is used in said reaction unit operating either in moving bed mode or in fixed bed mode.

13. A process for once-through conversion of a hydrocarbon feed comprising at least olefins containing 4 carbon atoms and at least olefins containing 5 carbon atoms, producing propylene, said process comprising preparing a spherical catalyst by a) preparing at least one emulsion formed from at least one porogen, which is a paraffinic kerosene cut containing 10 to 14 carbon atoms, formed from normal and isoparaffins, and having a boiling point in the range 220° C. to 350° C., said emulsion further comprising water and a surfactant, b) preparing a suspension formed from water, acid, a source of alumina, at least one zeolite and said emulsion prepared during step a), c) forming by drop coagulation, consisting of i) passing said suspension formed in b) into a draining pot constituted by nozzles each having an orifice calibrated to form droplets, ii) passing, in a downward movement, said droplets into a column containing an upper phase constituted by an organic phase and a lower phase constituted by a basic aqueous phase, the organic phase—aqueous phase interface being constituted by a surfactant, to harvest spherical beads, d) drying said beads and e) calcining said beads, passing said feed into at least one reaction unit provided with said catalyst in the form of spherical beads with a diameter in the range 1 to 3 mm, each of said spherical beads comprising at least one zeolite and at least one alumina-based, support and having a pore distribution such that the macroporous volume, measured by mercury porosimetry, is in the range 0.10 to 0.20 ml/g and the mesoporous volume, measured by mercury porosimetry, is in the range 0.25 to 0.35 ml/g, said catalyst further having a proportion of pore volume with pore size less than 20 nm in the range of 60-70%.

* * * * *